United States Patent [19]

Holtkamp

[11] Plant 4,268

[45] Jun. 20, 1978

[54] AFRICAN VIOLET PLANT

[76] Inventor: Reinhold Holtkamp, Wertherstrasse 112, 4294 Isselburg, Germany

[21] Appl. No.: 774,227

[22] Filed: Mar. 3, 1977

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

An African violet cultivar characterized by large pink, non-dropping flowers which have frilled edges, strong upright stems, with up to 10 flowers on each stem, and vigorous and uniform growth.

1 Drawing Figure

1

The present invention comprises a new and distinct cultivar of African violet plant, botanically known as *Saintpaulia ionantha,* and hereinafter referred to by the cultivar name Virginia. The new cultivar referred to during the breeding and selection process by No. b16/21 - 42/76, is a product of a planned breeding program. The female or seed parent, is the cultivar f III pink frill color 43-1, and was selected for breeding because of the frilled edges of its flower petals. The male, or pollen parent is designated XIX 4395 star, color 43-3, and was selected for breeding due to its upright flower stems and excellent array of leaves surrounding the flowers, which are on short and strong peduncles in number up to 10 flowers on each stem. These traits in combination were not present in previously available commercial cultivars, and the new cultivar possesses the desired characteristic of the parent cultivar.

The new cultivar was originated from a cross made in a controlled breeding program in Isselburg, Rhineland, Germany, and was discovered and selected as a flowering plant within the progeny of the stated cross by me in a controlled environment in Isselburg, Rhineland, Germany. Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Virginia, which in combination distinguish this African violet as a new and distinct cultivar:

1. Large pink flowers with frilled edges, with the flowers being non-dropping.
2. Strong upright flower stems with short peduncles.
3. Many flowers (up to ten) on each stem.
4. Vigorous growth.
5. Attractive saleable plant with the first flash of flowers.
6. Very uniform in growth.

The accompanying photographic drawing shows a typical specimen plant of the new cultivar, with the colors appearing in the photograph being as true as possible with color illustrations of this type.

2

In the following description, color references are made to the Munsell Limit Color Cascade chart, except where general color terms are referred to.

Botanical classification: *Saintpaulia ionantha,* Ramat. cv. Virginia.

Parentage:

*Male parent.*—XIX 4395 pink star, color 43-3.

*Female parent.*—f III pink frilled, color 43-1.

Propagation: The new cultivar holds its distinguishing characteristics through successive propagations by leaf cuttings and by division of shoots.

Plant: From 7 cm. to 10 cm. tall when grown in pots, and approximately 25–30 cm. in diameter when fully grown.

Leaves:

*General form.*—Round to oval.

*Diameter.*—60–70 mm.

*Texture.*—Soft and slightly hairy.

*Aspect.*—Velvety, slightly shiny.

*Veins.*—Underside, well pronounced, reddish, shiny.

*Color (upperside).*—Dark green, color 19-15.

*Color (underside).*—Brown-red.

*Petiole.*—Brown-reddish, hairy.

Flowers:

*Buds.*—Ball-shaped, approximately 2 mm. when small; before opening, 8–10 mm. in diameter.

*Sepals.*—Color: Brown. Calyx: Funnel-shaped. Aspect: Spear-shaped. Peduncle: Brown-red.

Individual flowers:

*Size.*—40–50 mm., almost flat.

*Color.*—Upperside: Pink, approximately 43-4 at center, becoming lighter at margins of flower. Underside: Pink, between 43-2 and 43-3.

*Borne.*—Flower stems have 8 to 10 flowers on strong peduncles.

*Shape.*—Every flower has 5 petals, 3 larger and 2 smaller, all having frilled edges; a few flowers tend to a small petal in the center.

*Corolla.*—The larger petals are 25 mm. long and 25 mm. wide; the small petals are 20 mm. long and 15 mm. wide.

*Arrangement.*—Strong and upright peduncle with up to 10 flowers.

*Flowering time.*—6–8 weeks after potting, depending on the time of the year, the plant is saleable with a nice decorative flowerhead.

Reproductive organs:

*Stamens.*—Two cells and two anthers; very few flowers have four cells.

*Anthers.*—Color 27-3.

*Arrangement.*—Two anthers in number, composed of two anther cells which give the appearance of four anthers in each flower.

*Filaments.*—4 mm. long., flat to round, color 24-2.

*Styles.*—Color 46-7, base of ovary light green, hairy.

*Pollen color.*—27-2.

Roots: Well developed roots are white when young, turning brown when older.

Disease resistance: Good, as experienced to date.

General observations: The new cultivar Virginia is a vigorous grower and comes to flower approximately 8 weeks after potting. The first flash of flowers forms a saleable plant with 5–8 flower stems and 6–10 blooms on each stem. The young flowers are always carried on strong upright stems, which tend to spread sideward for the following flowering until a full flowerhead is formed. The flowers remain, depending on temperatures, up to 6 weeks. The diameter of a full mature plant is 12–15 cm. The leaves spread radially outward from the flowerhead in the center of the plant.

I claim:

1. A new and distinct cultivar of African violet plant known by the cultivar name Virginia and particularly characterized as to uniqueness by the combined characteristics of large pink non-dropping flowers with frilled edges; strong upright flower stems with short peduncles; up to ten flowers on each stem; vigorous and uniform growth; saleability with the first flash of flowers, and its full flowerhead on second flowering.

* * * * *

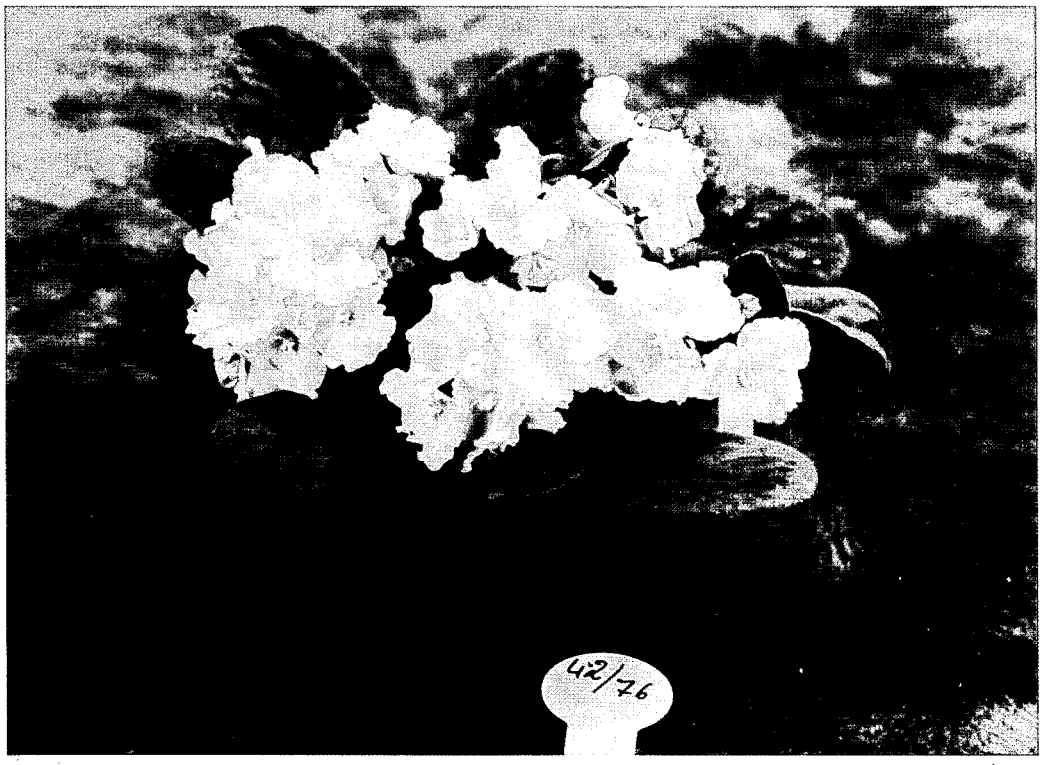
42/76